US00PP36070P2

(12) United States Plant Patent
Hansen

(10) Patent No.: US PP36,070 P2
(45) Date of Patent: Aug. 13, 2024

(54) **X *MANGAVE* PLANT NAMED 'Touch of Frost'**

(50) Latin Name: **x *Mangave* times x *Agave* hybrid**
Varietal Denomination: Touch of Frost

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,762

(22) Filed: Jan. 22, 2024

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP34,270 P2 * 5/2022 Hansen ..... Plt./373

* cited by examiner

*Primary Examiner* — Karen M Redden

(57) ABSTRACT

A new and unique x *Mangave* plant named 'Touch of Frost' is characterized by moderate to slow growth rate, compact habit, and lanceolate foliage with glaucous blue-green margins, light blue-chartreuse centers, a narrow creamy-white margin edge, with small, sharp, firm mucro, and flexible marginal teeth that become firm as they mature. The new plant has a moderate to slow growth rate. The new plant is suitable as a potted houseplant plant, as a container plant for the patio or garden, and for the garden planted in the landscape.

1 Drawing Sheet

Botanical classification: x *Mangave* times x *Agave* hybrid.
Variety denomination: 'Touch of Frost'.

STATEMENT REGARDING PRIOR DISCLOSURES UNDER 37 CFR 1.77(b)(6)

No plants of x *Mangave* 'Touch of Frost' have been sold or offered for sale in this country or anywhere in the world, nor has any disclosure of the new plant been made more than one year prior to the filing date of this application and such disclosure within one year was either derived directly or indirectly from the inventor.

BACKGROUND OF THE INVENTION

The present invention relates to the new and distinct x *Mangave* plant, x *Mangave* 'Touch of Frost' discovered on Feb. 11, 2021, by the inventor at a wholesale perennial nursery in Zeeland, Michigan, USA as a whole plant mutation of x *Mangave* 'Frosted Elegance' U.S. Plant Pat. No. 32,289. Through trials at the same nursery, the plant was referred to by the breeder code 21-sp-MANG-1016C prior to naming. The new plant has been successfully asexually propagated by shoot tip tissue culture in 2024 at the same nursery in Zeeland, Michigan. This asexual propagation method has been found to produce stable and identical plants that maintain all the unique characteristics of the original plant in successive generations.

BRIEF SUMMARY OF THE INVENTION

X *Mangave* 'Touch of Frost' differs from its parent as well as all other *Manfreda, Agave,* and x *Mangave* known to the applicant. The parent has a similar habit without the creamy-white marginal variegation on the leaves per plant. The new plant has glaucous blue-green margins and light blue-chartreuse center and a cream-white marginal variegation.

The most similar known X *Mangave* cultivar known to the inventor are: 'Blue Dart' (not patented), 'Blazing Saddles' U.S. Plant Pat. No. 31,274, 'Desert Dawn' U.S. Plant Pat. No. 32,330, 'Racing Stripes' U.S. Plant Pat. application No. 31,251, 'Shadow Waltz' U.S. Plant Pat. No. 31,601 and 'Painted Desert' U.S. Plant Pat. No. 31,630.

'Blue Dart' is a larger plant with broader foliage, the foliage is thicker, has brown marginal teeth and apical spine, and lacks the lighter blue-green center band. 'Blazing Saddles' has a larger habit with foliage that is broader, more lustrous, less glaucous leaves with reddish spotting in high light intensity. 'Desert Dawn' has a larger habit, broader foliage, smaller marginal teeth, and less glaucous foliage that is more solid greyed-purple with a purple center stripe in high ultraviolet light. 'Racing Stripes' has a larger habit, leaves that are shiny deep green on the margins and chartreuse-yellow in the center midrib, and the larger teeth and apical spine are yellowish as the leaf expands and develops a cinnamon color when mature. 'Shadow Waltz' has narrow arching leaves with broad dark green margins and light green to chartreuse center. 'Painted Desert' has a larger more horizontal habit, foliage with more flexible marginal teeth, and lacks the semi-flexible mucro at the leaf apex and also has greyed-purple spotting on the leaf surfaces. None of the above comparison varieties have the narrow creamy-white marginal variegation.

The new plant is unique from all of these variegated *Agave*, x *Mangave* and *Manfreda*known to the inventor by the following combined traits:

1. Compact habit with lanceolate foliage;
2. Foliage has small semi-flexible marginal teeth becoming firm with maturity and firm sharp apical mucro;
3. Foliage has glaucous blue-green margins, a light blue-chartreuse center with a narrow creamy-white margin edge above blue-green below with a narrow creamy-white margin edge;
4. Moderate to slow growth rate;

BRIEF DESCRIPTION OF THE DRAWINGS

The photograph of the new plant demonstrates the overall appearance of the new plant including the unique traits of a three-year-old plant grown in a container initially in a greenhouse with supplemental water and fertilizer as needed. The colors are as accurate as reasonably possible with color reproductions. Ambient light spectrum, temperature, source, and direction may cause the appearance of minor variations in color.

DETAILED BOTANICAL DESCRIPTION

Figure 1:
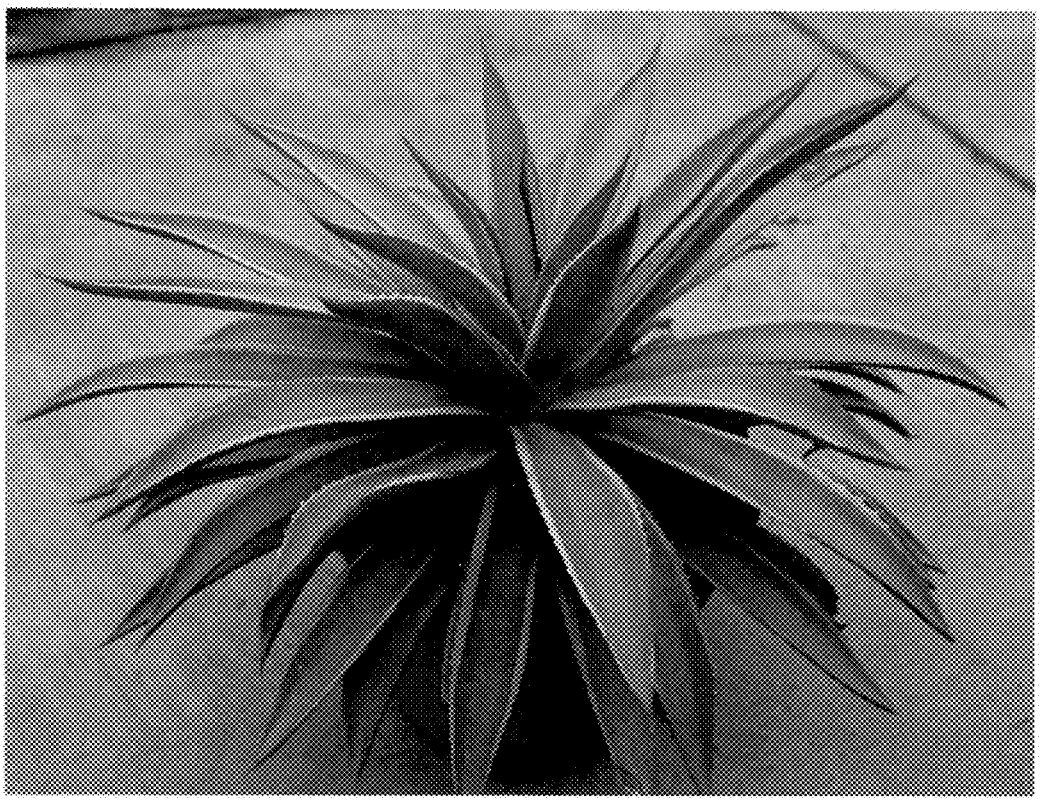
FIG. 1 shows the new plant from a side view.
Figure 2:
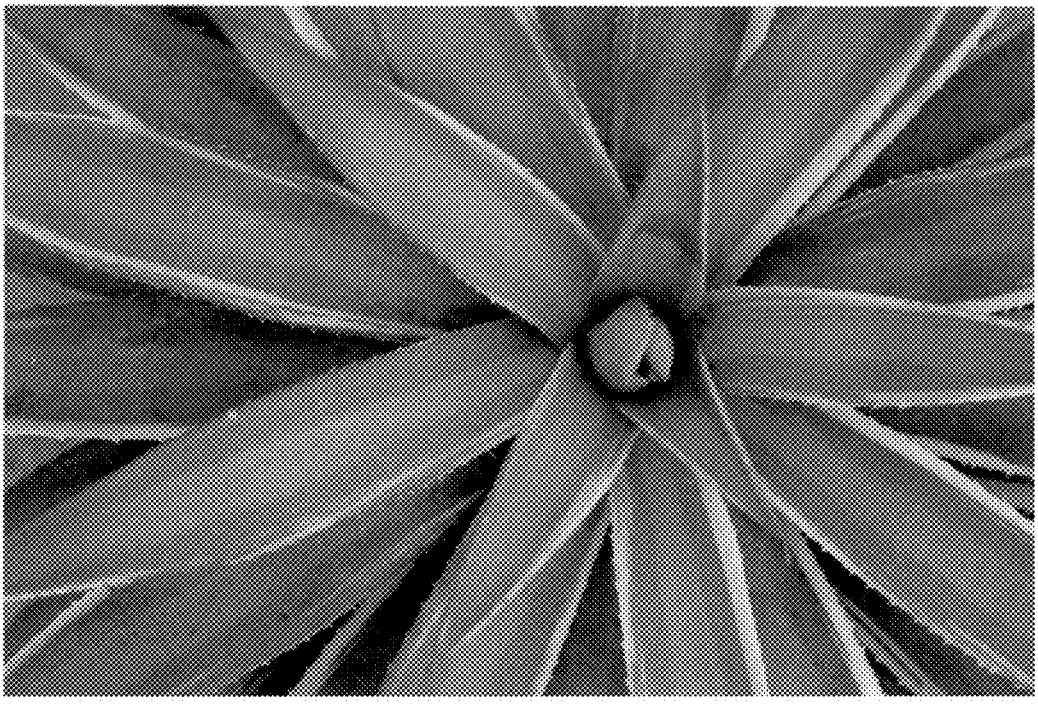
FIG. 2 shows a close-up of the foliage of the new plant from above.

The following descriptions and color references are based on the 2015 edition of The Royal Horticultural Society Colour Chart except where common dictionary terms are used. The new plant, x *Mangave* 'Touch of Frost', has not been observed under all possible environments.

The phenotype may vary slightly with different environmental conditions, such as temperature, light, fertility, moisture, and maturity levels, but without any change in the genotype. The following observations and size descriptions are of a three-year-old plant in a commercial wholesale greenhouse in Zeeland, Michigan with supplemental water and fertilizer as needed.

Botanical classification: *Agave* times x *Mangave* hybrid.

Variety denomination: 'Touch of Frost'.

Parentage: A whole plant mutation of 'Frosted Elegance'.

Propagation: Removal offsets, core division and sterile plant tissue culture.

Time to initiate roots from tissue culture: About 21 days.

Growth rate: Moderate.

Crop time: About 18 to 20 weeks to finish during lengthening spring days from an established 25 mm tissue culture plug to a 65 mm diameter container.

Rooting habit: Fleshy, lightly branching, with roots up to 15 cm long; color nearest R.H.S. 158C.

Plant shape and habit: Succulent herbaceous perennial with basal rosettes of about 60 fleshy leaves radially emerging and outwardly reaching from a central rhizome, producing a symmetrical rounded mound.

Plant size: Foliage height about 25 cm tall from the soil line to the top of the leaves and to about 49 cm wide at the widest point at the soil line.

Foliage description: Lanceolate; simple; sarcous; fibrous; glabrous; margins finely dentate with semi-flexible teeth; apex acute with firm mucro; base truncate, sessile, semi-clasping.

Leaf size: To about 22.5 cm long, about 42 mm wide near middle and 5 mm thick near base, average about 19 cm long, 35 mm wide and 4.5 mm thick; typically, bi-laterally symmetrical; glabrous and glaucous above and below; marginal teeth initially flexible becoming firm, curved backward slightly toward stem, about 2 mm long and 3 mm across at base about 6 mm apart; with terminal mucro.

Leaf variegation dimensions: Adaxial margin edge about 5 mm wide, light blue-chartreuse center about 15 mm wide, bluish-green intermediate region to about 11 mm wide; abaxial margin edge about 4 mm wide, light blue-chartreuse center very faint and only visible on some leaves about 10 mm wide, bluish-green intermediate region to about 22 mm wide.

Foliage fragrance: None observed.

Leaf blade color:

*Adaxial margin edge.*—Young expanding between R.H.S. 146D and R.H.S. N144A, mature nearest R.H.S. 11D.

*Abaxial margin edge.*—Young expanding between R.H.S. 146D and R.H.S. N144A, mature nearest R.H.S. 4C.

*Adaxial intermediate region.*—Young and mature margin between R.H.S. 188A and R.H.S. N138B.

*Abaxial intermediate region.*—Young and mature margin between R.H.S. 188A and R.H.S. N138B.

*Adaxial center region.*—Young and mature between R.H.S. 148B, R.H.S. N138C, and R.H.S. 191B.

*Abaxial center region* (*on mature leaves when distinguishable from the intermediate region*).—Between R.H.S. 146C, R.H.S. N138B, and R.H.S. 191B.

*Teeth.*—Abaxial and adaxial color variable on young foliage between R.H.S. 146D and R.H.S. N144A or nearest R.H.S. 184B; on mature foliage nearest R.H.S. 11D.

Mucro: Terminal spine; firm; straight; sharply pointed; about 3 mm long and 1 mm wide.

*Mucro color.*—Abaxial and adaxial on young foliage between R.H.S. 187A and R.H.S. 187B; on mature foliage nearest R.H.S. N187A.

Petiole: Sessile.

Veins: Parallel; not distinct.

Flowering and fruiting have not yet been observed.

Disease resistance: x *Mangave* 'Touch of Frost' has not been observed to be resistant to diseases common to other x *Mangave* beyond that which is normal for *Agave* or *Manfreda*.

Growth: The plant is xeromorphic and survives well with minimal water once established.

Hardiness at least from USDA zone 9 to 11. The full extent of winter hardiness has not been tested.

I claim:

1. A new and distinct cultivar of ornamental X *Mangave* plant named 'Touch of Frost' as herein described and illustrated.

* * * * *